(12) United States Patent
Dryden et al.

(10) Patent No.: US 10,145,823 B2
(45) Date of Patent: Dec. 4, 2018

(54) GAS CHROMATOGRAPHY (GC) COLUMN HEATER CONTROL USING MULTIPLE TEMPERATURE SENSORS

(71) Applicant: Agilent Technologies, Inc., Santa Clara, CA (US)

(72) Inventors: Paul C Dryden, Lincoln University, PA (US); Sammye Elizabeth Traudt, Middletown, DE (US); William H Wilson, Newark, DE (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 182 days.

(21) Appl. No.: 14/802,717

(22) Filed: Jul. 17, 2015

(65) Prior Publication Data

US 2016/0077063 A1    Mar. 17, 2016

Related U.S. Application Data

(60) Provisional application No. 62/073,394, filed on Oct. 31, 2014.

(51) Int. Cl.
*G01N 30/90* (2006.01)
*G01N 30/30* (2006.01)
*G01N 30/02* (2006.01)

(52) U.S. Cl.
CPC ....... *G01N 30/30* (2013.01); *G01N 2030/025* (2013.01); *G01N 2030/3007* (2013.01)

(58) Field of Classification Search
USPC ................................ 73/23.39, 23.35, 23.22
See application file for complete search history.

(56) References Cited

U.S. PATENT DOCUMENTS

| | | | |
|---|---|---|---|
| 3,213,596 A | 10/1965 | Gill | |
| 4,923,486 A * | 5/1990 | Rubey | G01N 30/30 95/87 |
| 5,782,964 A * | 7/1998 | Mustacich | G01N 30/30 73/23.25 |
| 5,808,178 A * | 9/1998 | Rounbehler | G01N 30/30 73/23.35 |
| 5,856,616 A * | 1/1999 | Maswadeh | G01N 30/16 422/89 |
| 5,939,614 A * | 8/1999 | Walters | G01N 30/30 422/88 |
| 6,029,498 A | 2/2000 | Walters et al. | |

(Continued)

FOREIGN PATENT DOCUMENTS

CN    101655483 A    2/2010
CN    101866190 A    10/2010

(Continued)

OTHER PUBLICATIONS

Wang, A., et al., "Gas Chromatography Using Resistive Heating Technology," Journal of Chromatography A, 2012, vol. 1261, pp. 46-57.

(Continued)

*Primary Examiner* — Eric S McCall
*Assistant Examiner* — Mohammed E Keramet-Amircola

(57) ABSTRACT

An apparatus for heating a GC column is described. The apparatus includes first and second temperature sensors. Temperature data are used to set power provided to a heating element of the apparatus.

20 Claims, 6 Drawing Sheets

(56) References Cited

U.S. PATENT DOCUMENTS

| | | | |
|---|---|---|---|
| 6,068,604 A * | 5/2000 | Krause | G01N 3/405 600/587 |
| 6,171,378 B1 | 1/2001 | Manginell et al. | |
| 6,454,840 B1 * | 9/2002 | Gellert | G01N 30/6095 55/DIG. 5 |
| 6,607,580 B1 * | 8/2003 | Hastings | G01N 30/30 95/87 |
| 6,666,907 B1 * | 12/2003 | Manginell | G01N 30/6095 73/23.36 |
| 6,966,212 B2 * | 11/2005 | Klee | G01N 30/12 73/23.41 |
| 7,396,468 B2 * | 7/2008 | Boyes | C07K 1/18 210/198.2 |
| 7,513,936 B2 | 4/2009 | Rogues | |
| 9,194,849 B2 | 11/2015 | Kanai et al. | |
| 2003/0228452 A1 | 12/2003 | Yu | |
| 2005/0184054 A1 | 8/2005 | Kachi et al. | |
| 2006/0283324 A1 * | 12/2006 | Roques | G01N 30/6095 96/101 |
| 2007/0266858 A1 * | 11/2007 | Alm | G01N 30/463 96/105 |
| 2009/0272270 A1 * | 11/2009 | McGill | B01J 20/205 96/101 |
| 2010/0044288 A1 | 2/2010 | Kitagawa | |
| 2011/0290233 A1 | 12/2011 | Iso et al. | |
| 2012/0160038 A1 * | 6/2012 | Wells | B01J 15/00 73/863.21 |
| 2013/0043380 A1 * | 2/2013 | Correale | G01N 1/2202 250/252.1 |
| 2013/0333444 A1 | 12/2013 | Kanai et al. | |
| 2014/0118742 A1 | 5/2014 | Rhodes | |
| 2014/0119993 A1 * | 5/2014 | Rhodes | G01N 21/766 422/52 |

FOREIGN PATENT DOCUMENTS

| | | |
|---|---|---|
| CN | 102680609 B | 2/2014 |
| JP | 05036363 U | 5/1993 |
| JP | 2004170155 A | 6/2004 |

OTHER PUBLICATIONS

PCT International Search Report and the Written Opinion of the International Searching Authority regarding PCT/US2015/041004 dated Oct. 19, 2015.

Partial Search Report dated Mar. 2, 2018, Application No. 15855286.9, 24 pages.

Perkin-Elmer, et al.,"Perkin-Elmer Model 226 Gas Chromatograph—Sophisticated, Simple and Automatic", Analytical Chemistry, vol. 36 ,Mar. 1, 1964 ,89A- 89A.

Extended Search Report dated Jun. 6, 2018, Application No. 15855286.9, 13 pages.

Han, et al. (2011). SOG-Si Purification Technology and Equipment, (1st ed.), Metallurgical Industry Press, 5 pages.

Li, et al., "A Design of Analyzer Temperature Monitoring System," Journal of Lanzhou Jiaotong University, vol. 27(1), Feb. 2008, pp. 110-113.

Zhao, Ji-Jing et al.,"Design of Temperature Controlling System for Electric Oven based on Double Single-Chip Microprocessor," Electronic Design Engineering, vol. 22(16), Aug. 2014, pp. 77-80, 84.

* cited by examiner

GAS CHROMATOGRAPHY (GC) COLUMN HEATER CONTROL USING MULTIPLE TEMPERATURE SENSORS

CROSS-REFERENCE TO RELATED APPLICATIONS

The present application claims priority under 35 U.S.C. § 119(e) from: U.S. Provisional Application No. 62/073,394 filed on Oct. 31, 2014, naming Paul Dryden, et al. as inventors. The entire disclosure of U.S. Provisional Patent Application No. 62/073,394 is specifically incorporated herein by reference.

BACKGROUND

In GC systems, the amount of time required for a chemical compound to traverse the entire length of a separation column ("column") is known as its retention time. One factor that contributes to the retention time of a chemical compound is the temperature of the separation column. Controlling the temperature of the column precisely from analysis to analysis is beneficial to provide repeatability in the retention time for a particular chemical compound, or analyte. In addition, programmatically changing the column temperature while the sample analytes are migrating through it can advantageously provide shorter analysis time and reduce peak broadening.

Precise control of the temperature of the column is, of course, important to the overall performance of the GC measurement. In many column temperature control systems, the temperature sensor does not measure the actual column temperature because it is located away from the column for various reasons. Although it is desirable for the column temperature to be constant along its length, no column heating system provides a completely isothermal environment. For the user of the GC apparatus, it is important that the thermal gradients along the length of the GC column are small and that analytes migrating through the column experience an effective temperature that provides the desired retention characteristics.

What is needed, therefore, is an apparatus that overcomes at least the drawbacks of known GC column heaters discussed above.

SUMMARY

In accordance with a representative embodiment, an apparatus comprises: a column heating apparatus; a first temperature sensor disposed adjacent to a gas chromatography column; and a second temperature sensor disposed in or above the column heating apparatus. A temperature of the gas chromatography column is altered based on temperature data from the first and second temperature sensors.

In accordance with a representative embodiment, the apparatus further comprises a first layer of thermal insulation disposed beneath the column heating apparatus and a second layer of thermal insulation. The second temperature sensor is disposed over, within, or beneath the second layer of thermal insulation.

In accordance with a representative embodiment, the column heating apparatus comprises: a first substrate; a heating element disposed over the first substrate; and a second substrate disposed over the column heating apparatus. The second substrate has a first side and a second side. The second side is configured to have the gas chromatography column in contact therewith. Heat from the column heating apparatus is transferred through the second substrate and substantially uniformly heats the gas chromatography column contacting the second substrate.

In accordance with another representative embodiment, an apparatus comprises: a first temperature sensor disposed adjacent to a gas chromatography column; and a second temperature sensor disposed in or above the column heating apparatus. A temperature of the gas chromatography column is altered based on temperature data from the first and second temperature sensors. The apparatus also comprises a controller configured to receive temperature data from the first and second temperature sensors. A power source is configured to receive control signals from the controller and to adjust electrical power to the column heating apparatus.

In accordance with yet another representative embodiment, a non-transitory computer readable medium storing a program, executable by a controller, for controlling a column heating apparatus, is disclosed. The computer readable medium comprises: a receiving code segment for receiving temperature data from a first temperature sensor and a second temperature sensor; a weighted average code segment for determining a weighted average from the temperature data; a comparison code segment for comparing the weighted average with a current set point; a proportional, integral derivative code segment for determining a temperature error; and a setting code segment for setting a power level to apply to a heating element from the temperature error.

In accordance with yet another representative embodiment, an apparatus for controlling a column heating apparatus is disclosed. The apparatus comprises: a controller configured to receive temperature data from a first temperature sensor and a second temperature sensor. The controller is further configured to execute programming operations. The programming operations comprise: determining a weighted average of temperature data from the temperature data; comparing the weighted average of the temperature data with a current set point temperature; determining a temperature error from the comparison of the weighted average of the temperature data and the current set point temperature; and adjusting a power level to apply to a heating element based on the determined temperature error.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

DEFINED TERMINOLOGY

Figure 1:
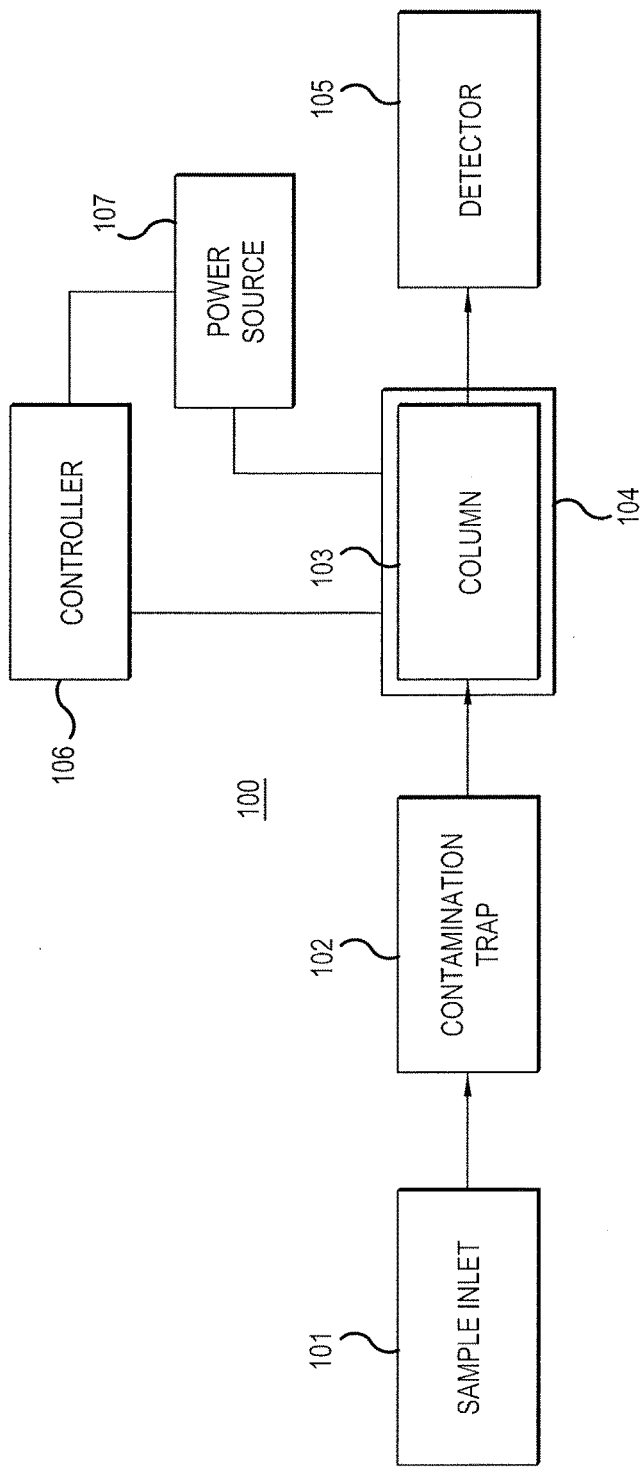
FIG. 1 is a simplified block diagram of a GC system in accordance with a representative embodiment.

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms 'a', 'an' and 'the' include both singular and plural referents, unless the context clearly dictates otherwise. Thus, for example, 'a device' includes one device and plural devices.

As used in the specification and appended claims, and in addition to their ordinary meanings, the terms 'substantial' or 'substantially' mean to with acceptable limits or degree. For example, 'substantially cancelled' means that one skilled in the art would consider the cancellation to be acceptable.

As used in the specification and the appended claims and in addition to its ordinary meaning, the term 'approximately' means to within an acceptable limit or amount to one having ordinary skill in the art. For example, 'approximately the same' means that one of ordinary skill in the art would consider the items being compared to be the same.

DETAILED DESCRIPTION

In the following detailed description, for purposes of explanation and not limitation, representative embodiments disclosing specific details are set forth in order to provide a thorough understanding of the present teachings. Descriptions of known systems, devices, materials, methods of operation and methods of manufacture may be omitted so as to avoid obscuring the description of the example embodiments. Nonetheless, systems, devices, materials and methods that are within the purview of one of ordinary skill in the art may be used in accordance with the representative embodiments.

Relative terms, such as "above," "below," "top," "bottom," "upper" and "lower" may be used to describe the various elements' relationships to one another, as illustrated in the accompanying drawings. These relative terms are intended to encompass different orientations of the device and/or elements in addition to the orientation depicted in the drawings. For example, if the device were inverted with respect to the view in the drawings, an element described as "above" another element, for example, would now be "below" that element. Similarly, if the device were rotated by 90° with respect to the view in the drawings, an element described "above" or "below" another element would now be "adjacent" to the other element; where "adjacent" means either abutting the other element, or having one or more layers, materials, structures, etc., between the elements. As used herein, an element "disposed over" or "disposed below" another element means the element is "adjacent to" the other element. "Directly adjacent" means abutting the other element.

Certain representative embodiments are directed to a gas chromatography (GC) column heating assembly. In accordance with a representative embodiment the GC column heating assembly comprises: a first temperature sensor disposed adjacent to a gas chromatography column; and a second temperature sensor disposed in or above the column heating apparatus. A temperature of the gas chromatography column is altered based on temperature data from the first and second temperature sensors. The system also comprises: a controller configured to receive temperature data from the first and second temperature sensors; and a power source configured to receive control signals from the controller and to adjust electrical power to the column heating apparatus to maintain a temperature of the GC column substantially at a desired value.

FIG. 1 is a simplified block diagram of a GC system 100 in accordance with a representative embodiment. Many aspects of the GC system 100 are known to one of ordinary skill in the art. As such, details of certain known components of the GC system 100 are omitted. In certain instances representative examples of known components that may be implemented are noted, but are presented for illustration and are, in no way, intended to be limiting.

The GC system 100 comprises a sample inlet 101. The sample inlet 101 is fluidically coupled to a contaminant trap 102. The contaminant trap 102 is fluidically coupled to a column 103, which may be one of a variety of columns useful in gas chromatography. In an embodiment, the contaminant trap 102 may be as described in concurrently filed, commonly owned U.S. patent application Ser. No. 14/057,022 (filed Oct. 18, 2013), the disclosure of which is specifically incorporated herein by reference. The contaminant trap 102 is a microfluidic contaminant trap configured to trap contaminants in the sample from the sample inlet 101 and to prevent the trapped contaminants from reaching the column 103. It is noted that the inclusion of contaminant trap 102 is merely illustrative, and the present teachings are contemplated for use in GC systems that do not comprise a contaminant trap, or that do not comprise a microfluidic contaminant trap as described in the application referenced immediately above.

The column 103 separates the components of a chemical sample. The column 103 may be a capillary column comprising a piece of fused silica or metal tubing (not shown) with a coating on the inner portions of the tubing or packed with particles that interact with the sample from sample inlet 101 to separate the components of the chemical sample.

The column 103 is provided in contact with a column temperature control apparatus 104, which will be described more fully below in connection with representative embodiments. By virtue of the column temperature control apparatus 104, the retention time is controlled, while the uniformity of the heating of the column 103 is comparatively improved. Furthermore, in certain embodiments, the column 103 can be cooled in a comparatively thorough manner, ultimately improving repeatability of the retention time of an analyte and analysis cycle time compared to known GC systems. These and other benefits of the column temperature control apparatus 104 are described more fully below in connection with representative embodiments.

The column 103 is connected to a detector 105, which detects the presence and frequently the quantity of the components separated by the column 103. Generally, the detector 105 is a known GC detector such as a flame ionization detector (FID), a mass spectrometer detector (MSD), a thermal conductivity detector (TCD), an electron capture detector (ECD), a nitrogen phosphorus detector (NPD), a sulfur chemiluminescence detector (SCD), a nitrogen chemiluminescence detector (NCD), a pulsed flame photometric detector (PFPD), a helium ionization detector (HID), or a flame photometric detector (FPD).

The GC system 100 also comprises a controller 106 and a power source 107. The controller 106 may be one of a plurality of controllers (not shown) of the GC system 100, or may be the sole controller of the GC system. Presently, the function of the controller 106 with respect to maintaining the heating of the column 103 by the column temperature control apparatus 104 is described. Other functions of the controller 106 or of other controllers are not germane to the present teachings and are not described.

Generally, the controller 106 can be implemented in numerous ways (e.g., such as with dedicated hardware) to perform various functions discussed herein. A "processor" is one example of a controller, which employs one or more microprocessors that may be programmed using a computer readable medium (software (e.g., microcode)) to perform various functions discussed herein. The controller 106 may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, microcontrollers, application specific integrated circuits (ASICs), and field-programmable gate arrays (FPGAs).

In various implementations, the controller 106 may be associated with one or more storage media (generically referred to herein as "memory," e.g., volatile and non-volatile computer memory such as random-access memory (RAM), read-only memory (ROM), programmable read-only memory (PROM), electrically programmable read-only memory (EPROM), electrically erasable and programmable read only memory (EEPROM), universal serial bus (USB) drive, floppy disks, compact disks, optical disks, magnetic tape, etc.). In some implementations, the storage media may be encoded with one or more programs that, when executed on the controller 106, perform at least some of the functions discussed herein. Various storage media may be fixed within the controller 106 or may be transportable, such that the one or more programs stored thereon can be loaded into a processor or controller so as to implement various aspects of the present teachings discussed herein. The terms "program" or "computer program" are used herein in a generic sense to refer to any type of computer code (e.g., software or microcode) that can be employed to program the controller 106.

As described more fully below in connection with FIGS. 3 and 4, the controller 106 is configured to receive temperature data from at least two temperature sensors (not shown in FIG. 1), and based on the temperature data, is configured to provide control signals to the power source 107. The power source 107 is one of a number of known electrical power sources and is configured to adjust the power of the column temperature control apparatus 104 to maintain the temperature of the column 103 at approximately a desired temperature.

Figure 2A:
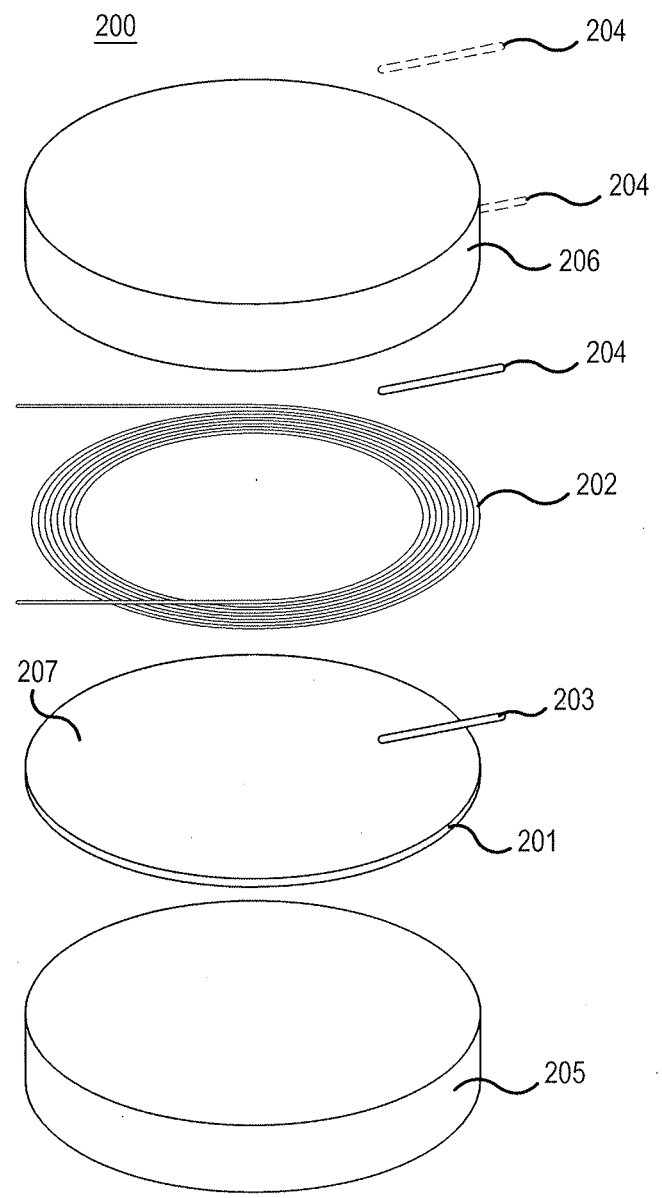
FIG. 2A shows an exploded view of a column heating assembly in accordance with a representative embodiment.

FIG. 2A shows an exploded view of a column temperature control apparatus 200 ("sometimes referred to as "apparatus") in accordance with a representative embodiment. Notably, the column temperature control apparatus 200 of the present embodiment is contemplated for use as the column temperature control apparatus 104 in GC system 100 described herein.

The column temperature control apparatus 200 comprises a column heating apparatus 201 configured to have a GC column 202 disposed over a surface 207. The GC column 202 is contemplated for use as the column 103 described in connection with representative embodiments of FIG. 1.

The column temperature control apparatus 200 additionally comprises a first temperature sensor 203 and a second temperature sensor 204. The first temperature sensor 203 is disposed in the first column heating apparatus 201. Alternatively, the first temperature sensor 203 may be disposed over the first column heating apparatus 201. The first temperature sensor 203 is illustratively embedded in the column heating apparatus 201, such as described below in connection with the representative embodiments of FIG. 2B, and in commonly owned U.S. Provisional Application 62/050,125, filed on Sep. 13, 2014, naming Sammye E. Traudt, et al. as inventors. The entire disclosure of this application is specifically incorporated herein by reference.

FIG. 2A depicts two different representative orientations for the second temperature sensor 204. A first layer of thermal insulation 205 is disposed beneath the column heating apparatus 201, and a layer of thermal insulation 206 is disposed above the GC column 202 and the second temperature sensor 204. In one embodiment, the second temperature sensor 204 may be disposed over the GC column 202 and below the layer 206 of thermal insulation as shown. In another embodiment, the second temperature sensor 204 may be disposed over the layer of thermal insulation 206. These temperature sensor locations are designed to reflect real-time temperature gradients that are not captured in prior art GC systems.

Preferably, the first temperature sensor 203 and second temperature sensor 204 are either devices such as a thermocouple, or a platinum resistance thermometer (PRT). The first and second temperature sensors 203, 204 must respond quickly enough to detect changes in their thermal environments. Notably, the first temperature sensor 203 must provide data to the controller that tracks the relatively rapid temperature changes in the column heating apparatus. Depending on the location of the heating element and its relative location to the second temperature sensor 204, the second temperature sensor 204 may be in a thermal environment that experiences slower changes in temperatures. Consequently, temperature changes in the GC column environment may be reflected in measurements from the first temperature sensor 203 prior to detection at the second temperature sensor 204

The first and second layers of thermal insulation 205, 206 are made of a material suitable to provide ample thermal insulation without interfering with the performance of the GC system. Illustratively, the first and second layers of thermal insulation 205, 206 are made of a glass fabric material having a thickness of approximately 0.25 in., and can be provided as "blankets" to improve conformance of the first and second layers of thermal insulation 205, 206 to the outer surfaces of the column heating apparatus 201 and the GC column 202 with which they contact. Alternatively, the first and second layers of thermal insulation 205, 206 may comprise other types of insulation including, but not limited to fiberglass, glass cloth, basalt, and the like. The material selected for the first and second layers of thermal insulation 205, 206 generally needs to provide a sufficient thermal barrier between the column heating apparatus 201 and the ambient environment during a GC run, while being capable to be cooled thoroughly and quickly after the GC run.

As described more fully in the present disclosure, the first and second temperature sensors 203, 204 provide data to controller 106 and a determination is made regarding the power provided by the power source 107 to the column temperature control apparatus 104, which comprises the column heating apparatus 201. By controlling the power provided to the column heating apparatus 201 based on temperature values from both first and second temperature sensors 203, 204, the temperature of the GC column 202 can be more accurately controlled compared to known methods. Notably, by locating the first temperature sensor 203 within the or on top of the column heating apparatus 201, comparatively rapid feedback about the temperature of the column heating apparatus 201 can be provided to the controller 106. In one embodiment, the first temperature sensor 203 is in physical contact with the column heating apparatus 201 which is designed to facilitate rapid changes in temperature in response to changes in the power applied to its heating element 213 (not shown in FIG. 2A) contained within the column heating apparatus 201. By contrast, because of the greater relative distance from the heating element 213, the second temperature sensor 204 is more thermally isolated. Consequently, changes in temperature originating from power modulation of the heating element will be detected by the second temperature sensor only after temperature information flows across the GC column 202 and any intervening layers between the heating element and the second temperature sensor 204.

Figure 2B:
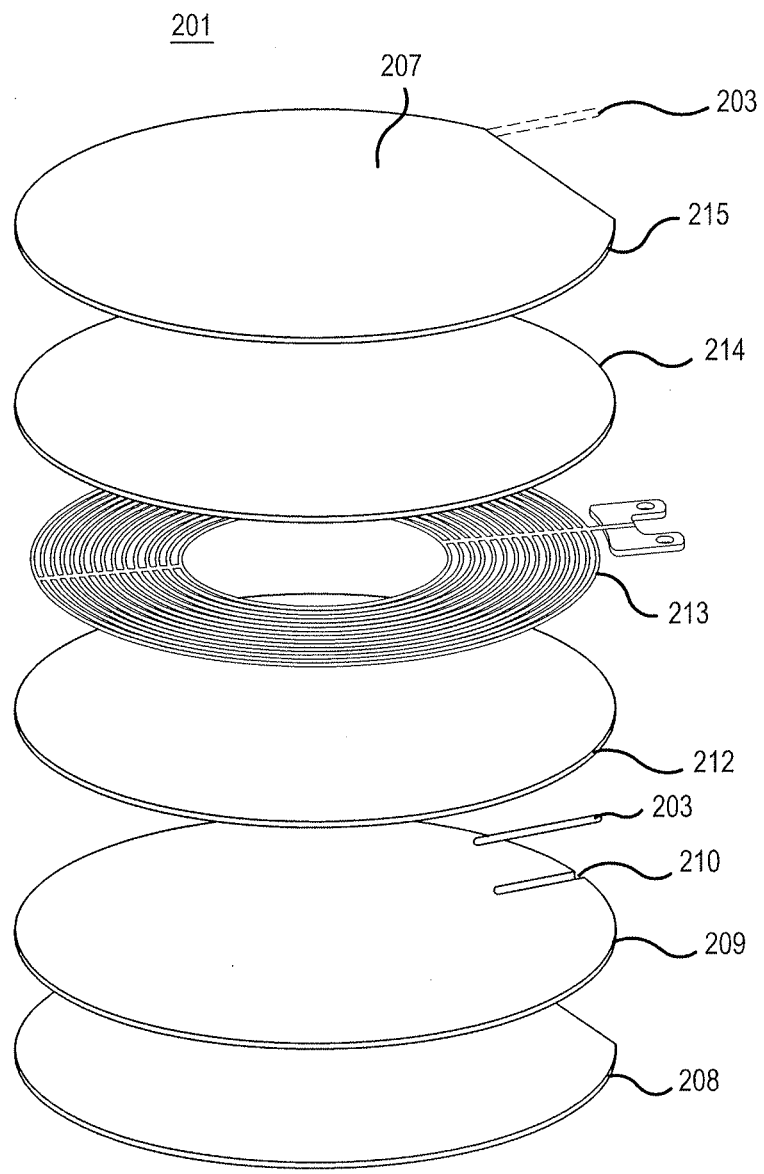
FIG. 2B shows an exploded view a column heating apparatus in accordance with a representative embodiment.

Moreover, locating the second temperature sensor 204 at the interface of the GC column 202 and the second layer of thermal insulation 205 allows for a measure of the temperature on the side of the GC column 202 opposing the side of the GC column adjacent to the surface 207, through which heat from the heating element 213 (not shown in FIG. 2A) of the column heating apparatus 201 flows. As such, locating the first and second temperature sensors 203, 204 as depicted in the representative embodiment of FIG. 2A provides a real-time indication of the thermal gradient from the column heating apparatus 201 to the side of the GC column 202 furthest from the column heating apparatus 201. FIG. 2B shows an exploded view of the column heating apparatus 201 depicting two representative locations of the first temperature sensor 203 within column heating apparatus 201. The column heating apparatus 201 comprises a first substrate 208, which is substantially planar. A spacer layer 209 is optionally disposed over the first substrate 208.

A recess 210 is provided in the spacer layer 209, and, in some embodiments, receives the first temperature sensor 203. In other embodiments, the first temperature sensor 203 can be located between an intervening layer 214 and second substrate 215. While some degree of benefit may be realized by mounting the first temperature sensor 203 in other places within the GC column temperature control apparatus 200, locating the first temperature sensor 203 in close proximity to the heating element 213 is beneficial for heater control.

Preferably, the first temperature sensor 203 is located in between the GC column 202 and the heating element 213. Illustratively, the first temperature sensor 203 may be located between an intervening layer 214 and the second substrate 215. Alternatively, the first temperature sensor 203 may be located on an "outer" side (i.e., beneath the first substrate 208 or above the second substrate 215).

A heating element 213 is disposed between an optional intervening layer 212 and an optional intervening layer 214 (referred to below as intervening layer 214). The intervening layers 212, 214 are generally made from the same material. The intervening layers 212, 214 may also be selected to act as electrical insulators between the heating element 213 and the first substrate 208 and a second substrate 215. Like the first substrate 208, the second substrate 215 is substantially planar. The second substrate 215 is configured to have the GC column (not shown in FIG. 2B) in thermal contact therewith. Illustratively, the GC column is disposed over the surface 207 of the second substrate 215, and heat from the heating element 213 is transferred through the second substrate 215 to the GC column. As can be appreciated from a review of FIG. 2B, the surface 207 is substantially planar.

The first and second substrates 208, 215 may comprise single layer or multiple layers of the same or different materials. As described more fully below, the column heating apparatus 201 substantially uniformly heats the GC column contacting the second substrate 215.

As should be appreciated by one of ordinary skill in the art, the "thermal mass" of an object is a measure of its capacity to store thermal energy (i.e., heat). As such, a material that has a comparatively low thermal mass will require less heat in order to change temperature than one of comparatively high thermal mass. As described more fully below, in order to enable faster heating and cooling, the materials selected for the first and second substrates 208, 215 of the column heating apparatus 201 have a comparatively low thermal mass.

Thermal mass (with units of J/K) is the product of the specific heat of the material, $c_p$, and the mass of the object, m. For convenience, thermal mass can be further specified as the product of the density, $\rho$, of the material, a surface area, $A_s$, and a thickness, t, normal to the surface area. Combining, thermal mass can be expressed as:

$$\text{thermal mass} = (\rho c_p t A_s)$$

Since the surface area of the column heating apparatus 201 is fixed based on the size of the column to be heated, the surface area is viewed as a constant for this discussion. The remaining terms are examined further. The term, $\rho c_p$, is also known as the volumetric heat capacity of the material and is an intrinsic property of the material. To minimize thermal mass, this term should be minimized. According to a representative embodiments, materials for the second substrate 215 or the first and second substrates 208, 215 have a volumetric heat capacity less than approximately $$3.0 \times 10^6 \frac{J}{m^3 K} \text{ at } 25° \text{ C}.$$

The selection of material for the second substrate 215 or the first and second substrates 208, 215 is additionally bound by mechanical stiffness, low thermal gradients, and resistance to thermal deformation. These bounds are particularly important in determining the minimum thickness of material required for the second substrate 215 or the first and second substrates 208, 215. Along with thermal mass, these are not independent characteristics, so choice of materials is made considering all of them. The ultimate goal is to achieve low thermal gradients across the surface 207 of second substrate 215 while achieving a relatively low thermal mass for first and second substrates 208 and 215 to enable faster heating and cooling.

Thermal gradients across the second substrate 215 or across the first and second substrates 208, 215 result from different parts of the substrates being in different thermal environments. The heating element 213, for instance, does not have a completely homogenous thermal profile. In addition, the outer edges of the first and second substrates 208, 215 will typically have more exposure to the ambient temperature environment. As such, thermal gradients can exist across the first and second substrates 208, 215. Gradients are reduced when the material chosen for the first and second substrates has low resistance to heat flow, that is, a high thermal conductivity, k. It is desirable, therefore, to have a material with comparatively high thermal conductivity, particularly for the second substrate 215, so that the surface 207 that touches the GC column is substantially uniform in temperature. According to a representative embodiments, materials for the second substrate 215 or the first and second substrates 208, 215 have a thermal conductivity greater than approximately $$100 \frac{W}{mK} \text{ at } 25° C.$$

The first and second substrates, 208 and 215, provide mechanical structure for the column heating apparatus 201. Notably, the first and second substrates 208, 215 provide ample support for the various relatively non-rigid components of the column heating apparatus 201 as well as the GC column 202 and the second temperature sensor 204. Beneficially, materials chosen for the first and second substrates 208, 215 are sufficiently stiff to provide such adequate support. The stiffness of a material is related to its elastic modulus (or Young's Modulus), E. If a material has a high elastic modulus, then less of it (e.g., a thinner piece of it) is necessary to provide the same stiffness as a material with a lower elastic modulus. It is beneficial, therefore, to have a material with a high elastic modulus so that less (thermal) mass of material is required to achieve adequate stiffness. According to a representative embodiments, materials for the first and second substrates 208, 215 have a Young's Modulus greater than approximately 100 GPa. In addition to stiffness, the first and second substrates, 208 and 215 must maintain surface flatness in order to hold the heating element 213 in contact with the second substrate 215, and the GC column 202 in direct contact with the surface 207, or in indirect contact with the surface 207 (i.e., with an intervening layer (not shown) between the GC column 202 and the surface 207). Issues in flatness may occur due to deformation or "buckling" from rapid temperature changes. If large thermal gradients exist in a component such as, for example, when the component is cooled asymmetrically, sections of the component will want to grow due to thermal expansion while other sections will want to remain fixed. In the worst case, this can cause buckling or fracture.

The likelihood of mechanical deformation due to thermal expansion can be minimized by choosing a material with a high thermal conductivity, k, low thermal expansion coefficient, a, or both. A material with high thermal conductivity resists the formation of large thermal gradients within the material. Materials with low thermal expansion do not grow very much even under significant thermal gradients. Choosing materials with a high thermal conductivity, low thermal expansion coefficient, or both, allows for the use of less material (e.g., a thinner piece of it) and therefore less thermal mass while providing adequate resistance to buckling. According to a representative embodiments, materials for the second substrate 215 or the first and second substrates 208, 215 have a ratio of thermal conductivity to coefficient of thermal expansion greater than approximately $$25 \frac{W}{m(ppm)} \text{ at } 25° C.$$

Another consideration in the selection of the material for the second substrate 215, or the first and second substrates 208, 215 is the electrical insulative properties of the material. Beneficially, the material is substantially electrically insulating to avoid having to add an additional material in the stack of the column heating apparatus 201 to perform this function.

Finally, it is important to select a material for the second substrate 215, or the first and second substrates 208, 215 that is operative in the column heating apparatus 201 at temperatures greater than approximately 450° C.

Table 1 presents a summary of some of the factors to be considered in selection of the material for the second substrate 215, or the first and second substrates 208, 215.

TABLE 1

| Issue Addressed | Parameter | Maximize or Minimize Parameter |
|---|---|---|
| Thermal Mass | $\rho c_p$ (Volumetric Heat Capacity) | Minimize |
| Thermal Gradients | k (Thermal Conductivity) | Maximize |
| Buckling/CTE | $\frac{k}{\alpha}$ (Thermal Conductivity/Coefficient of Thermal Expansion) | Maximize |
| Mechanical Stiffness | E (Young's Modulus) | Maximize |

In a representative embodiment, the second substrate 215 comprises silicon. Generally, the silicon layer that forms the second substrate 215 is illustratively monocrystalline silicon or polycrystalline silicon, and has a thickness of approximately 0.3 to 1.5 mm. Illustratively, the second substrate 215 comprises <1,0,0> silicon having a thickness of approximately 0.675 mm. In a representative embodiment, first substrate 208 is illustratively monocrystalline silicon or polycrystalline silicon. The first substrate 208 may comprise a <1,0,0> silicon wafer having a thickness of approximately 0.675 mm, and the second substrate 215 comprises two <1,0,0> Si wafers having a thickness of approximately 0.675 mm each. The use of two wafers for second substrate 215 provides somewhat improved retention time repeatability. Notably, the second substrate 215 does not require special polishing or doping. The first substrate 208 may be made of the same material and to the same specifications as the second substrate 215.

It is noted that the use of silicon for the second substrate 215, or the first and second substrates 208, 215 is merely illustrative. More generally, the materials selected for the second substrate 215, or the first and second substrates 208, 215 are selected to have a volumetric heat capacity ($\rho c_p$) less than approximately $$3.0 \times 10^6 \frac{J}{m^3 K} \text{ at } 25° C.;$$

a thermal conductivity (k) greater than approximately $$100 \frac{W}{mK} \text{ at } 25° C.;$$

a ratio of thermal conductivity to coefficient of thermal expansion $$\left(\frac{k}{\alpha}\right)$$

greater than approximately $$25 \frac{W}{m\{ppm\}} \text{ at } 25° C.;$$

and a Young's Modulus (E) greater than approximately 100 GPa.

These physical characteristic are desired in order to achieve faster heating and cooling of the column heating apparatus 201 within several bounds including low thermal mass, mechanical stiffness, low thermal gradients and resistance to deformation. Table 2 compares these four characteristics across a range of materials.

Therefore, aluminum, magnesium, silver, zinc, and gold are not preferable materials for the second substrate 215, or the first and second substrates 208, 215.

The material selected for the second substrate 215, or the first and second substrates 208, 215 additionally should have a Young's Modulus greater than approximately 100 GPa. Therefore graphite is not a preferable material for the second substrate 215, or the first and second substrates 208, 215.

Based on the analysis above, illustrative materials that can be used for the second substrate 215, or the first and second substrates 208, 215 comprise silicon, aluminum nitride, diamond, silicon carbide, tungsten, molybdenum, alloys of tungsten (particularly with copper), alloys of molybdenum (particularly with copper), and combinations thereof.

TABLE 2

| Parameter | Silicon | Aluminum | Aluminum Nitride | Pyrex | Diamond | Silicon Carbide | Copper | Tungsten | 85% Tungsten 15% Copper | Molybdenum |
|---|---|---|---|---|---|---|---|---|---|---|
| $\rho c_p (J/10^6 cm^3 K)$ | 1.64 | 2.43 | 2.44 | 1.67 | 1.80 | 2.05 | 3.42 | 2.58 | 2.85 | 2.55 |
| k(W/mK) | 130 | 205 | 140 | 1 | 1000 | 300 | 401 | 174 | 215 | 138 |
| $\frac{k}{\alpha}$(W/m-ppm) | 50 | 8.91 | 31.1 | 0.25 | 847 | 108 | 23.6 | 40.5 | 28.9 | 27.6 |
| E(GPa) | 130 | 69 | 308 | 64 | 1220 | 450 | 117 | 400 | 310 | 329 |

Based on the foregoing, the material selected for the second substrate 215, or the first and second substrates 208, 215 should have a volumetric heat capacity less than approximately $$3.0 \times 10^6 \frac{J}{cm^3 K} \text{ at } 25° C.$$

Therefore, copper, alumina, nichrome, stainless steel, nickel, sapphire, silicon nitride, tungsten carbide, beryllium oxide, brass, bronze, aluminum brass, iron, and beryllium are not preferable materials for the second substrate 215, or the first and second substrates 208, 215.

The material selected for the second substrate 215, or the first and second substrates 208, 215 should have a thermal conductivity greater than approximately $$100 \frac{W}{mK} \text{ at } 25° C.$$

This specification additionally eliminates Therefore, Pyrex glass, mica, titanium, quartz glass, gallium arsenide, germanium, boron nitride, zirconium oxide, boron carbide, indium phosphide, niobium, rhenium, and tantalum are not preferable materials for the second substrate 215, or the first and second substrates 208, 215.

The material selected for the second substrate 215, or the first and second substrates 208, 215 additionally should have the ratio of thermal conductivity, k, to the coefficient of thermal expansion, $\alpha$, that is greater than approximately $$25 \frac{W}{m\{ppm\}} \text{ at } 25° C. \text{ (at } 25° C.).$$

In one representative embodiment, a heating element 213 is disposed between the intervening layers 212, 214. The intervening layers 212, 214 are generally made from the same material, and each have a second comparatively low thermal mass. Moreover, the intervening layers 212, 214 are each made from a material that is electrically insulating. Notably, if the first and second substrates 208, 215 are electrically insulating, then the intervening layers 212, 214 may be omitted. However, if the material of the intervening layers 212, 214 can become more electrically conducting at comparatively high temperatures (e.g., silicon), then electrical insulation is needed between the heating element and first and second substrates 208, 215. As such, in a representative embodiment in which first and second substrates comprise silicon, the intervening layers 212, 214 may be needed. Notably, however, in another representative embodiment, rather than including the intervening layers 212, 214, the sides of the first and second substrates 208, 215 facing the heating element may be coated with a layer of glass or other dielectric to perform this insulating function.

In a representative embodiment, the intervening layers 212, 214 each comprise mica, which are of sheet silicate (phyllosilicate) minerals. Generally, mica materials are $X_2Y_{4-6}Z_8O_{20}(OH,F)_4$ in which X is K, Na, or Ca or less commonly Ba, Rb, or Cs; Y is Al, Mg, or Fe or less commonly Mn, Cr, Ti, Li, etc.; Z is chiefly Si or Al, but also may include $Fe^{3+}$ or Ti. The use of mica for the intervening layers 212, 214 is merely illustrative, and other materials having similar thermal mass, electrical conductivity, and resistance to mechanical distortion due to rapid temperature change as mica are contemplated. For example, fabrics such as fiberglass, and basalt provide the desired properties.

The heating element 213 is illustratively a resistive heating element, such as a wire heater or a foil heater. Other types of heating elements are contemplated. As should be appreciated, the heating element is beneficially quite thin, and thereby does not substantially interfere with the desirably flat nature of each of the layers of the column heating apparatus 200. With known thin film fabrication methods, such comparatively thin heating elements that are within the purview of one of ordinary skill in the art are contemplated.

Figure 2C:
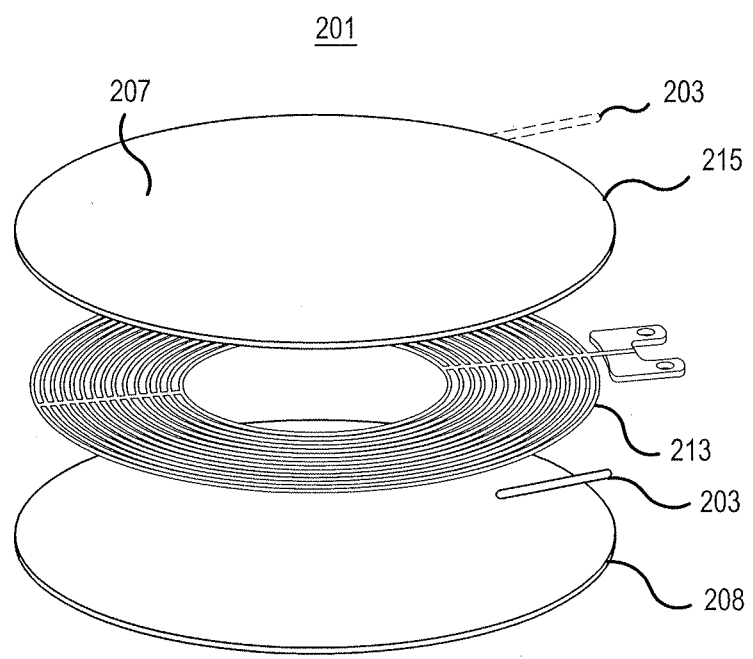
FIG. 2C shows an exploded view a column heating apparatus in accordance with a representative embodiment.

FIG. 2C shows an exploded view of column heating apparatus 201 in accordance with another representative embodiment. Many aspects of the column heating apparatus 201 are substantially identical to those of column heating apparatus 201 described above in connection with FIG. 2B. As such, many details of various features that are common to those of column heating apparatus 201 in FIG. 2B are not repeated. Notably, the various characteristics of the common elements of the column heating apparatus 201 are the same. For example, when made of the same material (e.g., silicon), the comparative magnitudes of the thermal masses of the first and second substrates 208, 215 relative to other components of the column heating apparatus 201 are the same as those described above.

The column heating apparatus 201 comprises the first substrate 208 having heating element 213 disposed thereover. Notably, however, the column heating apparatus 201 of FIG. 2C does not comprise spacer and intervening layers 209, 212, 214, which were noted above as being optional.

FIG. 2C depicts two representative locations of other first temperature sensor in an alternate embodiment of the column heating apparatus 201. In one embodiment, the first temperature sensor 203 is disposed over the first substrate 208 and beneath the heating element 213. In another embodiment the first temperature sensor 203 is located between heating element 213 and second substrate 215. As noted above, while some degree of benefit may be realized by mounting the first temperature sensor 203 in other places within the GC column temperature control apparatus 200 locating the first temperature sensor 203 in close proximity to the heating element 213 is beneficial for heater control.

The column heating apparatus 201 also comprises second substrate 215 disposed over the heating element 213. The second substrate 215 is configured to have a GC column (not shown in FIG. 2C) in direct contact therewith or indirect contact therewith (i.e., with an intervening layer (not shown) between the GC column and the second substrate 215. Illustratively, the GC column is disposed over the surface 207 of the second substrate 215, and heat from heating element 213 is transferred through the second substrate 215 as described above in connection with the representative embodiments of FIG. 2B. The first and second substrates 208, 215 may comprise single layer or multiple layers of the same or different materials. Through the heat distribution of the second substrate 215 described above, the apparatus 201 substantially uniformly heats the GC column contacting the second substrate 215.

The GC column temperature control apparatus 200 comprises the first temperature sensor 203 disposed within or directly adjacent to a column heating apparatus 201 comprising a heating element 213 as shown in FIGS. 2B and 2C. Locating the first temperature sensor 203 within or adjacent to the heating element 213 enables comparatively rapid feedback about the temperature of the heating element 213 to be provided to the controller 106. Moreover, locating the second temperature sensor 204 on the opposite side of the GC column from the heating element captures real-time temperature gradients.

Figure 3:
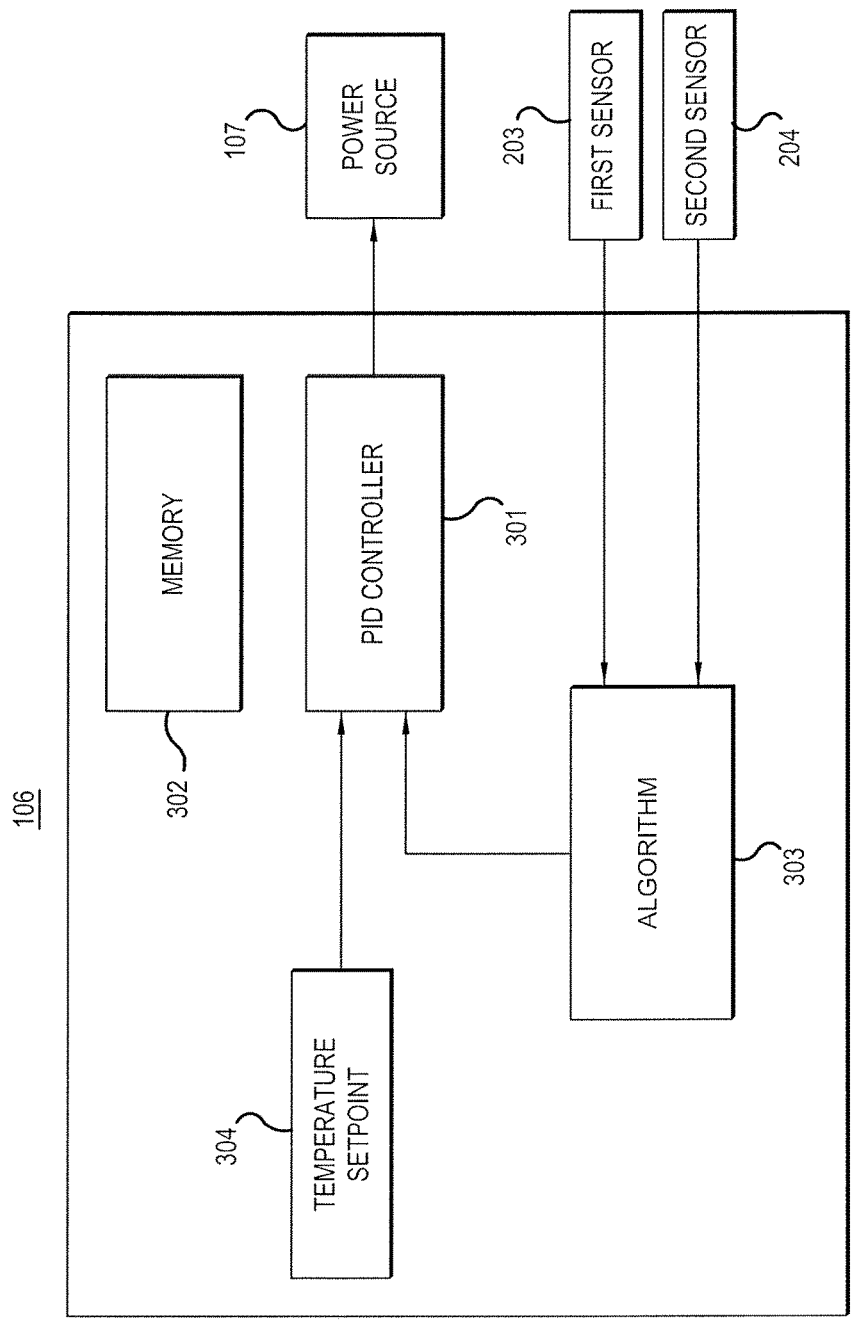
FIG. 3 shows a simplified block diagram of a controller in accordance with a representative embodiment.

FIG. 3 shows a simplified block diagram of the controller 106 in accordance with a representative embodiment. The simplified block diagram depicts those components of the controller 106 that are useful in determining the required power to be provided to the heating element 213 in order to maintain the temperature of the GC column, or the immediate surroundings of the GC column, or both, at substantially the desired level. Notably, other components of the controller 106, including other hardware and firmware that do not relate to the temperature control of the GC column, are not shown or described.

The controller 106 comprises a proportional-integral-derivative (PID) controller 301. The PID controller 301 may be instantiated in software, a microcontroller or programmable logic device (PLD), such as a field programmable gate array (FPGA), or other similar device. The PID controller 301 is instantiated with a PID controller algorithm that involves three separate constant parameters, and is often referred to as a three-term control: the proportional, integral and derivative values. The algorithm is presented in the form of software or firmware, or a combination of both. As described more fully below, the PID controller algorithm in the form of a program (instructional code) can be stored in a memory 302 or other computer readable medium and can cause the HD controller 301 to determine the set point for the power source in order to heat a GC column (e.g., GC column 202) to a desired level. Notably, in representative embodiments in which the PID controller 301 is instantiated in software, it may be stored in memory 302.

The controller 106 also includes a mathematical processing component or algorithm 303, which is configured to receive temperature data from the first temperature sensor 203 and from the second temperature sensor 204, and calculate an improved estimate of the true column temperature than either the first temperature sensor 203 or the second temperature sensor 204 could provide alone. –. The algorithm block 303 illustratively comprises a processor instantiated in hardware, firmware, or software, or a combination thereof. Alternatively, the algorithm block 303 comprises analog circuitry, such as a resistor-pair. In a preferred embodiment, the algorithm is used to determine the weighted average of the two temperature sensors. Calculating the weighted average of the data from the first and second temperature sensors can be effected by multiplying the temperature from the first temperature sensor 203 by a value (X) and the temperature from the second temperature sensor 204 by a value (1–X). Notably, the value of X is determined by optimizing ambient rejection and is described more fully below. The weighted average provides an estimate of the temperature near the GC column 202, and by properly selecting the value of X, this estimate can be substantially accurate in the time frame through continuous collection and interpretation of data from the first and second temperature sensors 203, 204. While the weighted average algorithm is described, other approaches to processing the temperature input data and deriving an estimated column temperature are contemplated.

Generally, the algorithm block 303 is configured to determine a temperature value that is as close as possible to the actual column temperature over a range of conditions. One condition that will vary in a real-world situation is ambient temperature. The temperature at the first temperature sensor 203 and at the GC column 202 can vary differently as ambient temperature changes. When using only the value of the first temperature sensor 203 as an input, the PID controller 301 can only compensate for the effect of ambient temperature shifts near the location of the first temperature sensor 203. Due to thermal resistances in the system, the compensation made will not exactly compensate for the effect of ambient temperature at the GC column 202. This will result in a slight overall change in column temperature. As a sample peak traverses the column it will therefore see a slightly different average temperature and the resulting peak elution time will shift slightly. The column temperature change will usually be a fraction of the ambient temperature change. To maintain repeatable peak elution times (which will allow for the easiest analyte identification) it is optimal to keep this fraction as small as possible. "Ambient rejection" is a term given to describe the relationship between ambient temperature changes and effective column temperature changes and is given by the change in ambient temperature divided by the resulting change in column temperature. Ambient rejection can be either positive or negative. In any case, it is desirable to maximize the absolute value of the ambient rejection. Ambient rejection in a good GC system is usually on the order of 100:1.

By using a properly selected weighted average of the first temperature sensor 203 and a second temperature sensor 204, the PID controller 301 can more accurately compensate for ambient shifts at the column because the actual column temperature is better approximated. By measuring the actual column temperature through the elution times of compounds through the GC column 202 under varying ambient condition, one can determine how effective including the second temperature sensor 204 is in improving ambient rejection.

Beneficially, the value of X is selected so that results in ambient temperature variation having no effect on compound retention. Experimentally, X can be substantially optimized by repeatedly injecting the same sample under the same nominal GC conditions (e.g., oven, inlet, detector temperature and pressure set-points) and observing the shift in retention time or retention index as X and ambient temperature are varied. Retention index, a relative measure of retention for a given analyte, can be used to determine an effective column temperature. The change in ambient temperature divided by the change in effective column temperature gives the ambient rejection of the thermal system.

The controller 106 comprises a temperature set-point module 304, which provides the current power set point to the PID controller 301. The algorithm block 303 provides the weighted average value from the most recent calculation to the PID controller 301. The PID controller 301 calculates the difference between the set-point temperature from the temperature set-point module 304 and the weighted average value to determine a temperature error. The PID controller algorithm adds P times the temperature error, adds I times the integral of the temperature error over the time since the last temperature data were received from the first and second temperature sensors 203, 204, and then adds D times the derivative of the temperature error. There are various means of determining useful values of P, I and D for each iteration of calculating the temperature error and, ultimately, determining the value of the power applied by the power source 107 to the heating element 213.

The temperature error is the instantaneous error, and thus, is independent of what it was before, or what it will be after. The integral, however, is the running sum of all of the temperature errors since a particular point in time, such as when the zone was turned on, or when the temperature was near the set-point. The derivative is based on the current measurement and one or more of the previous measurements. In one embodiment, the derivative could be the change in temperature between the most-recent temperature error and the previous temperature error, measured a fixed time apart, divided by the time difference between the determinations of the two temperature errors. However, more sophisticated means of calculating the derivative may be needed, and are contemplated by the present teachings, to reduce the effects of noise. Notably, while the derivative can be computed from the difference between two measurements offset in time, this simple technique may be too sensitive to noise in the measurements and may give less than desirable control. There are numerous known ways to calculate a more noise-immune value for the derivative. For example, a least-squares fit of a function to multiple data points could be performed, and the derivative calculated from this function. Even though the multiple data points cover a period of time leading up to the current calculation, the computed derivative would be the estimate for a particular time within that period, for example, the middle of the period. Beneficially, the estimate of the derivative should be made for a time as close as possible to that of the most recent temperature measurement, either by using a small number of data points to fit the function, or by evaluating the function at a time corresponding to the time of the most recent measurement.

Once the PID controller 301 determines the new power level for the power source 107 to provide to the heating element 213, the power source 107 applies the new power level. Additional data are then gathered from the first and second temperature sensors 203, 204 and the process is repeated. Generally, the process is repeated prior to beginning the next measurement. Specifically, the interval between iterations (the elapsed time between temperature measurements) needs to be short enough to match the speed of the thermal response of the thermal zone. As is known, the thermal response represents a delay between when the applied power changes, and the time this change is sensed in the first and second temperature sensors 203, 204. The thermal response results, inter alia, from the combined effects of thermal resistance between the heater and sensor, and various thermal masses associated with the system. A fast system will have low thermal resistance or low thermal mass, or both.

Each time the temperature is measured, the PID calculation is performed and the heater power is adjusted to this new value. Of course, this can all be done in analog circuitry, in which case everything is continuous rather than discreet, and there is no interval.

Figure 4:
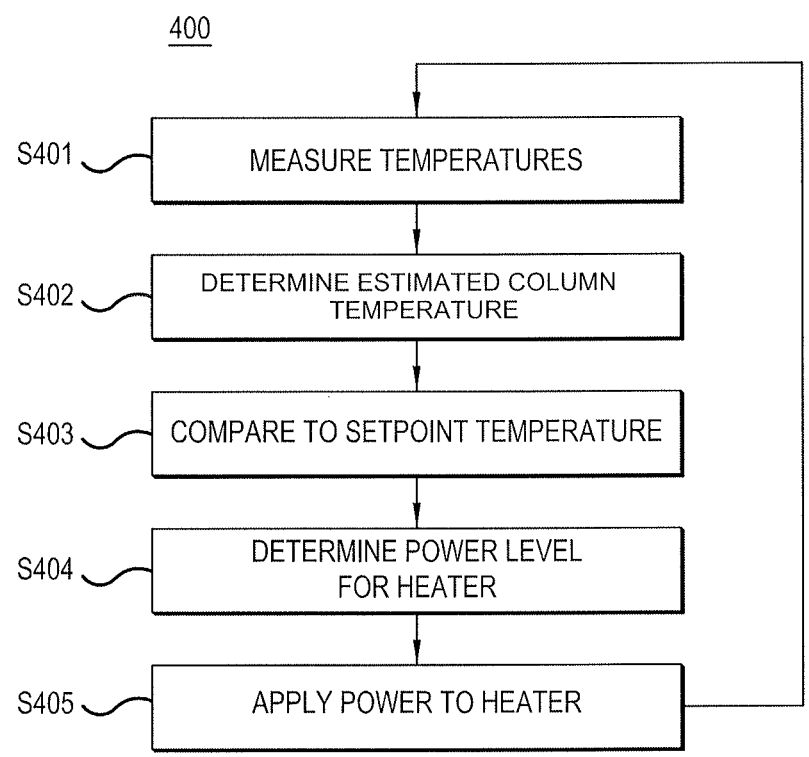
FIG. 4 shows a flow-chart of a method of controlling a temperature of a GC column in accordance with a representative embodiment.

FIG. 4 shows a flow-chart of a method 400 of controlling a temperature of a GC column in accordance with a representative embodiment. The method 400 is illustratively implemented in connection with the embodiments described above in connection with FIGS. 1-3. Notably, the method 400 may be carried out a number of ways through the hardware, software or firmware of the controller 106. In a representative embodiment, non-transitory computer readable medium storing a program is provided in the controller (e.g., in memory 302). This program includes code for effecting the method. In each part of the method below; different aspects of the code are disclosed. Such code is readily determined by one of ordinary skill in the art, and is not repeated in the interest of clarity of description of the present embodiments.

At S401, the method comprises measuring temperatures. As noted above, temperature measurements are made by the first and second temperature sensors 203, 204. A receiving code segment is provided in computer readable medium for receiving temperature data from the first temperature sensor 203 and the second temperature sensor 204.

At S402, the column temperature estimate is determined in the controller 106 as described above. In a preferred embodiment, a weighted average code segment is provided in computer readable medium for determining the weighted average temperature from the temperature data.

At S403, a comparison is made between the column temperature estimate and the current set point at the controller 106. A comparison code segment is provided in computer readable medium for comparing the column temperature estimate with a current set point temperature. Based on this comparison, a temperature error is determined at the PID controller 301. A proportional, integral derivative code segment is provided in computer readable medium for determining a temperature error.

At S404, as described above, the PID algorithm determines the new power level required to apply to the heating element 213. A setting code segment is provided in computer readable medium for setting a power level to apply to a heating element from the temperature error.

At S405, as described above, the power source 107 adjusts the power level applied to the heating element 213 based on the power level input from the PID controller. An adjusting code segment is provided in computer readable medium for adjusting the power level to apply to a heating element 213 based on the temperature error.

As shown, the process is repeated beginning at S401. As mentioned, this depends on how fast the thermal zone responds. Illustratively, thermal zones of representative embodiments are serviced 50 times per second. As is known, servicing includes measuring the temperature; using the temperature data to perform a PID calculation in the PID controller 301, and providing control signals to the power source 107 to change the power provided to the column temperature control apparatus 104 in GC system 100 described above.

In view of this disclosure it is noted that the methods and devices can be implemented in keeping with the present teachings. Further, the various components, materials, structures and parameters are included by way of illustration and example only and not in any limiting sense. In view of this disclosure, the present teachings can be implemented in other applications and components, materials, structures and equipment needed to implement these applications can be determined, while remaining within the scope of the appended claims.

The invention claimed is:

1. A gas chromatography column temperature control apparatus, comprising:
    a column heating apparatus;
    a first temperature sensor located within or directly adjacent to the column heating apparatus;
    a second temperature sensor disposed above the column heating apparatus; and
    a gas chromatography column disposed between the first temperature sensor and the second temperature sensor, wherein a temperature of the gas chromatography column is altered based on temperature data from the first and second temperature sensors.

2. An apparatus as claimed in claim 1, further comprising a first layer of thermal insulation disposed beneath the column heating apparatus and a second layer of thermal insulation, die second temperature sensor being disposed over, within, or beneath the second layer of thermal insulation.

3. An apparatus as claimed in claim 1, wherein the column heating apparatus comprises a first substrate; a heating element disposed over the first substrate; and a second substrate disposed over the column heating element, the second substrate having a first side and a second side, the second side configured to have the gas chromatography column in contact therewith, wherein beat from the column heating apparatus is transferred through the second substrate and substantially uniformly heats the gas chromatography column contacting the second substrate.

4. An apparatus as claimed in claim 3, wherein the second substrate comprises silicon.

5. An apparatus as claimed in claim 3, wherein the second substrate comprises monocrystalline silicon or polycrystalline silicon.

6. An apparatus as claimed in claim 3, wherein the first substrate comprises silicon.

7. An apparatus as claimed in claim 3, wherein the first substrate comprises monocrystalline silicon or polycrystalline silicon.

8. An apparatus as claimed in claim 3, the second substrate having: a volumetric heat capacity less than $$3.0 \times 10^6 \frac{J}{m^3 K} \text{ at } 25° \text{ C.};$$

a thermal conductivity greater than $$100 \frac{W}{mK} \text{ at } 25° \text{ C.};$$

a ratio of thermal conductivity to coefficient of thermal expansion greater than approximately $$25 \times 10^6 \frac{W}{m} \text{ at } 25° \text{ C.};$$

and a mechanical stiffness greater than 100 GPa.

9. An apparatus as claimed in claim 3, the second substrate comprising one of: aluminum nitride, diamond, silicon carbide, tungsten, molybdenum, an alloy of tungsten, an alloy of molybdenum, or a combination thereof.

10. An apparatus as claimed in claim 3, further comprising a spacer layer disposed between the heating element and the first substrate, the layer adapted to receive the first temperature sensor and to maintain the first temperature sensor adjacent to the heating element.

11. A temperature control system, comprising:
    a first temperature sensor disposed adjacent to a gas chromatography column; and
    a second temperature sensor disposed in or above the column heating apparatus;
    a controller configured to receive temperature data from the first and second temperature sensors and to output control signals based on the temperature data from the first and second temperature sensors; and
    a power source configured to receive control signals from the controller and to adjust electrical power to the column heating apparatus to alter the temperature of the gas chromatography column.

12. A system as claimed in claim 11, wherein the controller comprises a proportional, integral, derivative (PID) controller.

13. A system as claimed in claim 12, wherein the PID controller is configured to effect a first PID calculation based on the temperature data from the first temperature sensor, and to effect a second PID calculation based on the temperature data from the second temperature sensor.

14. A system as claimed in claim 13, wherein the second PID calculation is used to calculate and alter the first PID calculation.

15. A system as claimed in claim 12, wherein the PID controller is configured to effect a PID calculation based on a weighted average of temperature data from the first and second temperature sensors.

16. A system as claimed in claim 11, wherein a control signal based on the altered first PID calculation is provided to the power source.

17. A system for controlling, a column heating apparatus, the apparatus comprising:
- a controller configured to receive temperature data from a first temperature sensor and a second temperature sensor, the controller further configured to execute programming operations, comprising:
- determining an estimated column temperature from the temperature data;
- comparing the estimated column temperature with a current set point temperature;
- determining a temperature error from the comparison of the estimated column temperature and the current set point temperature; and
- adjusting a power level to apply to a heating element based on the determined temperature error.

18. A system as claimed in claim 17, wherein the estimated column temperature is calculated using data from both the first and second temperature sensors.

19. A system as claimed in claim 17, wherein the first temperature sensor is located closer to the heating element than the second temperature sensor.

20. A system as claimed in claim 17, wherein the current set point temperature is a function of the desired temperature of a gas chromatography column.

* * * * *

UNITED STATES PATENT AND TRADEMARK OFFICE
CERTIFICATE OF CORRECTION

PATENT NO. : 10,145,823 B2  
APPLICATION NO. : 14/802717  
DATED : December 4, 2018  
INVENTOR(S) : Paul C Dryden et al.

Page 1 of 1

It is certified that error appears in the above-identified patent and that said Letters Patent is hereby corrected as shown below:

In the Specification

In Column 6, Line 37, after "204" insert -- . --.

In Column 9, Line 43, delete "a," and insert -- α, --, therefor.

In Column 11, Line 4, delete " $25 \frac{W}{m\{ppm\}}$ " and insert -- $25 \frac{W}{m(ppm)}$ --, therefor.

In Column 11, Line 65, delete " $25 \frac{W}{m\{ppm\}}$ " and insert -- $25 \frac{W}{m(ppm)}$ --, therefor.

In Column 13, Line 29, after "embodiment" insert -- , --.

In Column 14, Line 20, delete "HD" and insert -- PID --, therefor.

In the Claims

In Column 17, Line 57, in Claim 2, delete "die" and insert -- the --, therefor.

In Column 17, Line 66, in Claim 3, delete "beat" and insert -- heat --, therefor.

In Column 19, Line 8, in Claim 17, delete "controlling," and insert -- controlling --, therefor.

Signed and Sealed this  
Twenty-second Day of January, 2019

Andrei Iancu  
*Director of the United States Patent and Trademark Office*